US010743827B2

(12) United States Patent
Kumar

(10) Patent No.: US 10,743,827 B2
(45) Date of Patent: Aug. 18, 2020

(54) ROBOTIC ARM WITH X-RAY SOURCE

(71) Applicant: General Electric Company, Schenectady, NY (US)

(72) Inventor: G. S. Sampath Kumar, Bangalore (IN)

(73) Assignee: General Electric Company, Schenectady, NY (US)

( * ) Notice: Subject to any disclaimer, the term of this patent is extended or adjusted under 35 U.S.C. 154(b) by 457 days.

(21) Appl. No.: 15/420,399

(22) Filed: Jan. 31, 2017

(65) Prior Publication Data

US 2018/0214100 A1    Aug. 2, 2018

(51) Int. Cl.
*A61B 6/00* (2006.01)
*H01J 37/02* (2006.01)

(52) U.S. Cl.
CPC .......... *A61B 6/4458* (2013.01); *A61B 6/4429* (2013.01); *A61B 6/465* (2013.01); *A61B 6/466* (2013.01); *A61B 6/467* (2013.01); *A61B 6/587* (2013.01); *A61B 6/588* (2013.01); *H01J 37/023* (2013.01); *G01N 2223/308* (2013.01); *G01N 2223/32* (2013.01); *G01N 2223/321* (2013.01)

(58) Field of Classification Search
CPC .. A61B 6/00; A61B 6/40; A61B 6/405; A61B 6/44; A61B 6/4411; A61B 6/4429; A61B 6/4452; A61B 6/4458; A61B 6/4476; A61B 6/4482; A61B 6/46; A61B 6/461; A61B 6/462; A61B 6/465–467; A61B 6/54; A61B 6/542; A61B 6/545; A61B 6/547; A61B 6/548; A61B 6/58; A61B 6/582; A61B 6/587–589; A61B 2560/00; A61B 2560/02; A61B 2560/0266; A61B 2560/04; A61B 2560/0431; A61B 2560/0437; A61B 2560/0443; H05G 1/00; H05G 1/02; H05G 1/26; H05G 1/30; G01N 2223/00; G01N 2223/30; G01N 2223/306; G01N 2223/308; G01N 2223/32; G01N 2223/321; H01J 35/00; H01J 35/02; H01J 37/00; H01J 37/02; H01J 37/023
See application file for complete search history.

(56) References Cited

U.S. PATENT DOCUMENTS

| | | | | |
|---|---|---|---|---|
| 2005/0058256 | A1* | 3/2005 | Beimler | A61B 6/08 378/162 |
| 2005/0234327 | A1* | 10/2005 | Saracen | A61B 6/0457 600/407 |
| 2009/0074151 | A1* | 3/2009 | Henderson | A61B 6/037 378/198 |
| 2009/0097612 | A1* | 4/2009 | Rauch | A61B 6/032 378/19 |
| 2010/0243924 | A1* | 9/2010 | Uchida | A61B 6/4464 250/522.1 |

FOREIGN PATENT DOCUMENTS

EP    1066794 A2 *  1/2001  .......... A61B 6/4464

* cited by examiner

*Primary Examiner* — Anastasia Midkiff

(57) ABSTRACT

An X-ray system includes a multiple degree of freedom robotic arm mounted to a surface of a radiology suite, the robotic arm having one or more telescoping arm members, an X-ray source mounted on an end effector of the multiple degree of freedom robotic arm, at least one X-ray detector, and a work station coupled to the robotic arm, X-ray source, and X-ray detector, wherein the work station is configured to compute robotic arm trajectories for at least one scanning procedure and to control the robotic arm, X-ray source, and X-ray detector to effect the at least one scanning procedure.

17 Claims, 6 Drawing Sheets

ROBOTIC ARM WITH X-RAY SOURCE

FIELD

The disclosed exemplary embodiments relate generally to X-ray systems, and more particularly to X-ray systems fixed to a structure.

BACKGROUND

A number of X-ray imaging systems of various designs are known and are presently in use. Such systems are generally based upon generation of X-rays that are directed toward a subject of interest. The X-rays traverse the subject and impinge on a detector, for example, a film, an imaging plate, or a portable cassette. The detector detects the X-rays, which are attenuated, scattered or absorbed by the intervening structures of the subject. In medical imaging contexts, for example, such systems may be used to visualize the internal structures, tissues and organs of a subject for the purpose screening or diagnosing ailments.

X-ray systems may be fixed or mobile. Fixed radiation systems generally utilize an X-ray source mounted to an overhead tube support. An exemplary overhead tube support X-ray system 100 is shown in FIG. 1. The overhead tube support typically includes a column 105 to which the X-ray source 110 is attached, coupled to an overhead rectangular bridge 115 that travels along a system of rails or tubes 120 oriented perpendicular to the bridge 115. A transport mechanism 125 coupled to the bridge 115 operates to move the column 105 along a longitudinal horizontal axis, while the rail system 120 allows the bridge 115 to travel along a lateral horizontal axis in the same plane. The rail system 120 typically includes a front rail 120a, a rear rail 120b, and a cable drape rail (not shown) mounted to a ceiling of a room or suite housing the fixed radiation system. In some installations, the overhead tube support system 100 may be mounted to a system of struts which are fixed to the ceiling.

The components of the overhead tube support can be expensive to produce and install. Positioning the X-ray source over a patient's anatomical features from a parked position of the overhead tube support system may be time consuming because of the longitudinal and lateral distances being traversed and the fixed speeds of motors used to drive the overhead tube support components. Furthermore, the overhead tube support system has a limited number of degrees of freedom, making imaging some aspects of a patient's anatomy difficult. It would be advantageous to provide an overhead fixed X-ray system that overcomes these and other disadvantages.

SUMMARY

The disclosed embodiments are directed to a robotic arm assembly suspended from a fixed location, having an end effector with an X-ray source attached. The robotic arm assembly may operate without an overhead tube suspension and may eliminate the need for a bridge and rail arrangement and any associated carriage or transport mechanisms. The robotic arm assembly may have sufficient articulation to provide patient coverage for fixed X-ray clinical procedures, including table and wall stand applications. The robotic arm assembly may have variable speed joints that provide faster X-ray source positioning compared to conventional systems.

The X-ray source may be positioned automatically or may also be positioned manually using a power assisted mode where sensors and motors at each joint sense an application of external force and respond with movement in the force direction while the force is being applied. The robotic arm assembly 300 may include sensors and may implement a slow down procedure or a stop and shutdown procedure when an unanticipated object is detected within a predefined work zone area of the robotic arm. The assembly 300 may include a system of collision detection sensors to avoid collisions with objects including the operator, the patient, clinical equipment, or any other obstacle that may be present in the environment. The collision sensors may be coupled to the work station for controlling the robotic arm 300 accordingly when a possible collision is detected.

The robotic arm assembly may support all types of fixed radiology imaging applications including over the table and wall stand applications. The robotic arm assembly movement to any point in space for any chosen field of view or source to image-receptor distance (SID) may be controlled by pre-set path definitions stored in the system or may be calculated before or during movement while accounting for an operator, the patient, any clinical equipment, or any other barrier or obstruction present in the radiology suite.

In at least one aspect, the disclosed embodiments are directed to an X-ray system including a multiple degree of freedom robotic arm mounted to a surface of a radiology suite, the robotic arm having one or more telescoping arm members, an X-ray source mounted on an end effector of the multiple degree of freedom robotic arm, at least one X-ray detector, and a work station coupled to the robotic arm, X-ray source, and X-ray detector, wherein the work station is configured to compute robotic arm trajectories for at least one scanning procedure and to control the robotic arm, X-ray source, and X-ray detector to effect the at least one scanning procedure.

The X-ray system may include one or more of a movable table and a movable wall stand in which the X-ray detector is mounted, and the work station may be further configured to control movement of the one or more of a movable table and a movable wall stand to effect the at least one scanning procedure.

The multiple degree of freedom robotic arm may be mounted to one or more of a ceiling, a wall, or a floor of the radiology suite.

The multiple degree of freedom robotic arm may include a plurality of joints providing six degrees of freedom.

The one or more telescoping arm members of the robotic arm may be independently extendable and retractable to provide an X-ray source coverage area corresponding to dimensions of the radiology suite.

The X-ray source may include an X-ray generator and an X-ray collimator.

The X-ray detector may include a digital radiography receiver panel with a two dimensional detection plane.

The X-ray detector may be configured to provide image data to the work station in real time.

The X-ray detector may be configured to store image data and output the image data when coupled to the work station.

The work station may be configured to provide signals for controlling a frequency and amount of radiation produced by the X-ray source during scanning operations.

The work station may be configured provide signals for controlling a sensitivity of the detector during scanning operations.

The work station may have an image processing capability for processing the signals from the detector to produce an output of 2D or 3D images from the scanning operations.

In at least one aspect, the disclosed embodiments are directed to a method of X-ray imaging including mounting a multiple degree of freedom robotic arm to a surface of a radiology suite, the robotic arm having one or more telescoping arm members, mounting an X-ray source on an end effector of the multiple degree of freedom robotic arm, providing at least one X-ray detector positioned to receive radiation produced by the X-ray source, and computing robotic arm trajectories for at least one scanning procedure and controlling the robotic arm, X-ray source, and X-ray detector to effect the at least one scanning procedure.

The method may include controlling movement of one or more of a movable table and a movable wall stand holding the detector to effect the at least one scanning procedure.

The method may also include independently extending and retracting one or more telescoping arm members of the robotic arm to provide an X-ray source coverage area corresponding to dimensions of the radiology suite.

The method may further include controlling a frequency and amount of radiation produced by the X-ray source during scanning operations.

The method may yet further include using the X-ray detector to provide image data to the work station in real time.

The method may still further include using the X-ray detector to store image data and output the image data when coupled to the work station.

The method may also include processing the signals from the X-ray detector to produce an output of 2D or 3D images from the scanning operations.

BRIEF DESCRIPTION OF THE DRAWINGS

The foregoing and other aspects of the disclosed embodiments are made more evident in the following Detailed Description, when read in conjunction with the attached Drawing Figures, wherein.

DETAILED DESCRIPTION

Figure 1:
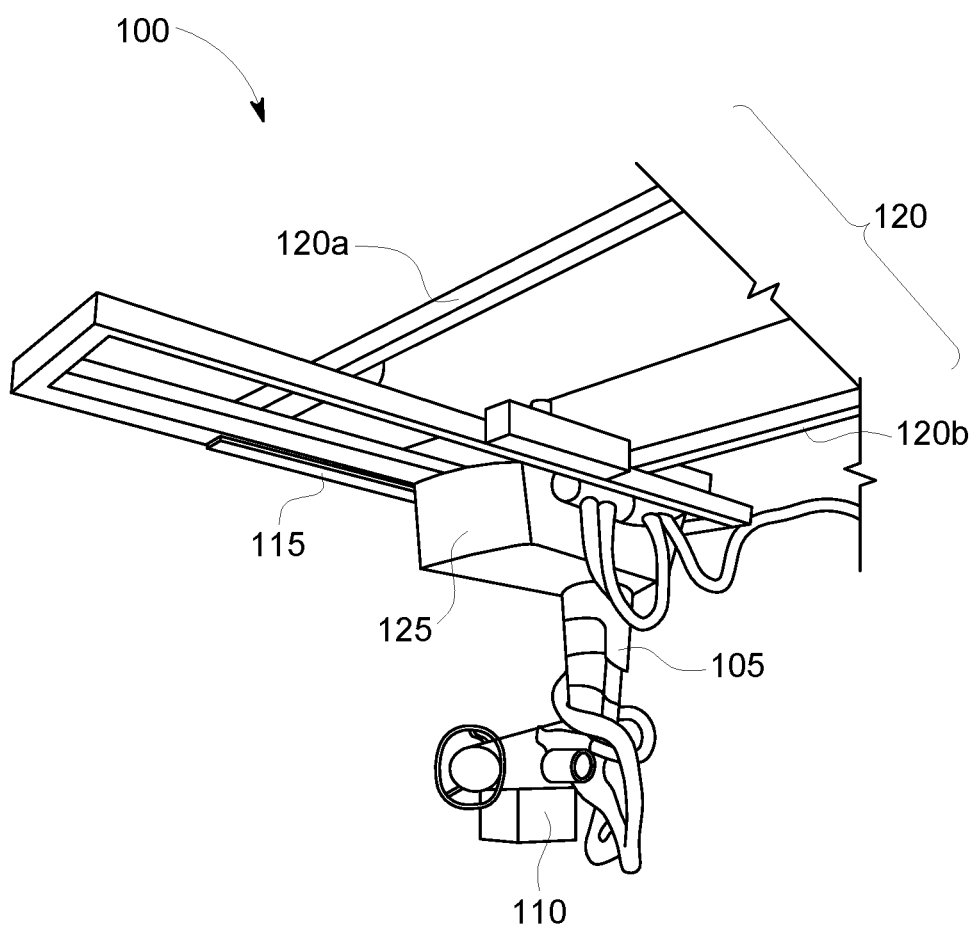
FIG. 1 shows a diagram of a prior art imaging system.
Figure 2:
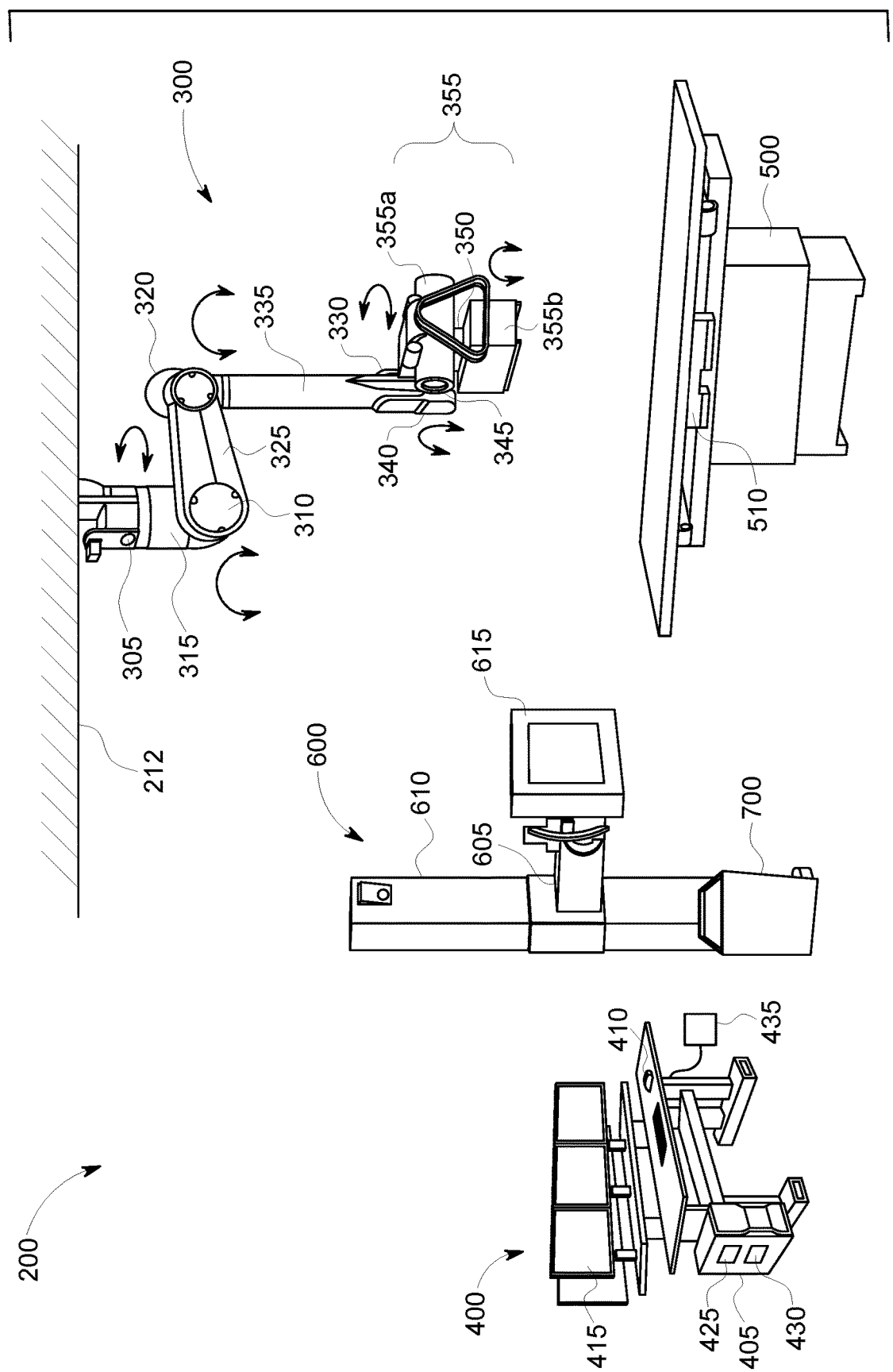
FIG. 2 shows an exemplary fixed X-ray system according to the disclosed embodiments.

FIG. 2 shows an exemplary fixed X-ray system 200 according to the disclosed embodiments. The exemplary system 200 may include a robotic arm 300, a work station 400, a table 500, a wall stand 600, and a detector 700. The robotic arm 300 may be mounted to a ceiling 212 of a radiology suite, however, it should be understood that the robotic arm may also be mounted to a wall or floor for certain applications. It should also be understood that the fixed X-ray system 200 may also include other components suitable for implementing the disclosed embodiments. The term radiology suite generally refers to a room or rooms which are configured for performing radiology procedures typically using X-ray imaging techniques. Exemplary radiology procedures may include but are not limited to Computed Tomography (CT), computerized axial tomography (CAT) scanning, and fluoroscopy.

The robotic arm 300 may have a number of joints and linking components, for example, a waist joint 305 defining a first axis. In at least one embodiment, the waist joint 305 may rotate from 0° to approximately 330°. The robotic arm 300 may also include a shoulder joint 310 defining a second axis and a base arm member 315 connecting the waist joint 305 and the shoulder joint 310. The shoulder joint may be rotatable from approximately 30° to approximately 210°. The robotic arm 300 may further include an elbow joint 320 defining a third axis and an upper arm member 325 connecting the shoulder joint 310 and the elbow joint 320. The elbow joint may have a rotational capability of between approximately 0° and approximately 160°. The robotic arm 300 may also include a first wrist joint 330 defining a fourth axis and a lower arm member 335 connecting the elbow joint 320 and the first wrist joint 330. In at least one embodiment, the first wrist joint 330 may rotate from approximately 0° to approximately 330°. A second wrist joint 340 may be included as part of the robotic arm 300, defining a fifth axis, and a third wrist joint 345 may also be included defining a sixth axis. The second wrist joint 340 may rotate from approximately 20° to approximately 60° while the third wrist joint 345 may rotate from approximately 0° to approximately 180°. The third wrist joint 345 may include an end effector 350 on which an X-ray source 355, for example, including an X-ray generator 355a and a collimator 335b, may be mounted. It should be understood that the rotational capabilities of the various joints are exemplary and may include any suitable rotational ranges.

The fixed X-ray system may include a collision avoidance capability. For example, each joint 305, 310, 320, 330, 340, 345 and end effector 350 may be configured to detect collisions and proximities of other objects and may include one or more collision sensors, proximity sensors or any other sensors suitable for avoiding collisions and contact with objects including humans, clinical equipment or structures within the radiology suite. The various components of the robotic arm 300 may also include one or more mechanical stops for preventing motion beyond a specified parameter. The sensors may be coupled to the work station for controlling the robotic arm 300 accordingly when a possible collision is detected.

Figure 3:
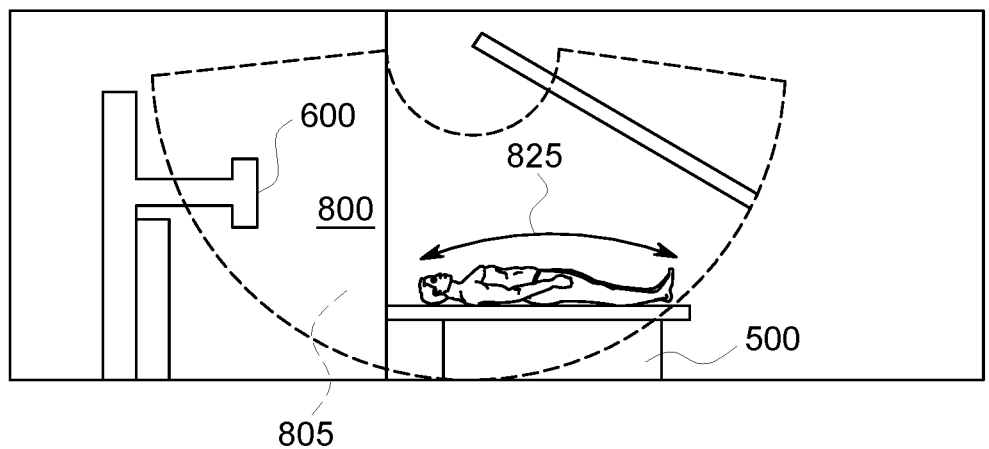
FIG. 3 shows a side view of an exemplary radiology suite coverage area provided by the disclosed embodiments.
Figure 4:
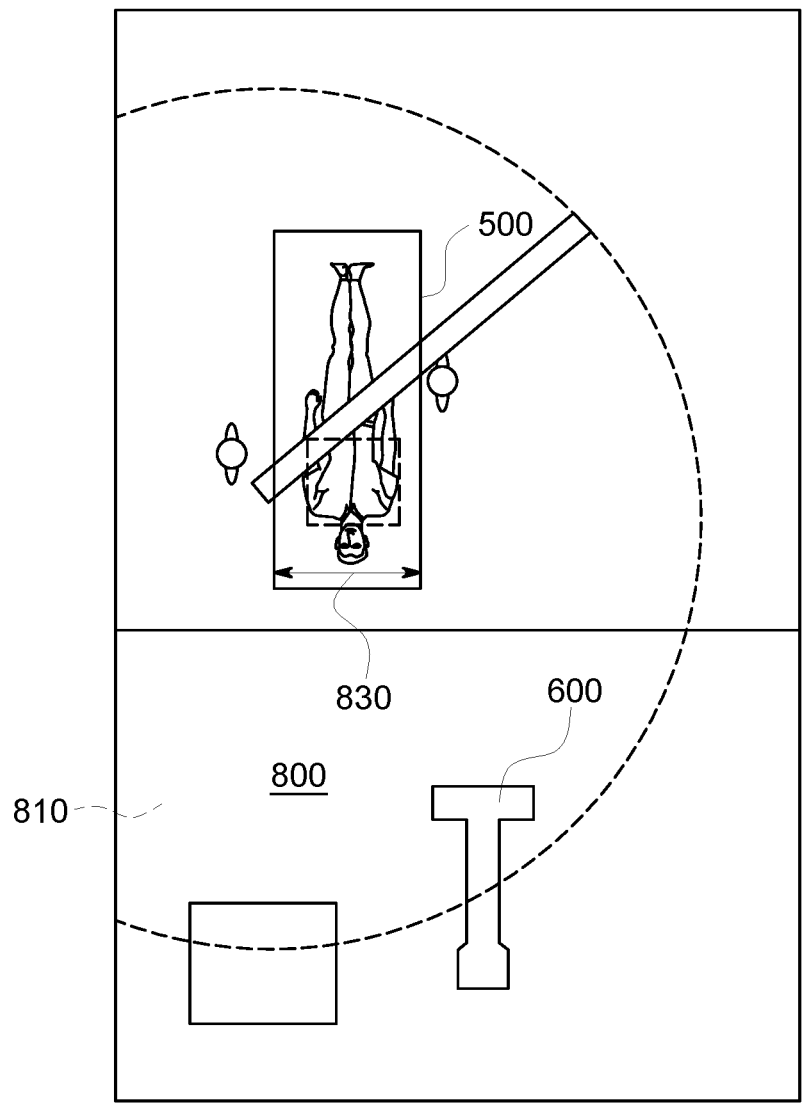
FIG. 4 shows a top view of the exemplary radiology suite coverage area provided by the disclosed embodiments.

One or more of the base arm member 315, upper arm member 325, and lower arm member 335 may each have an independent telescoping capability, that is, each arm member 315, 325 may include a mechanism that may provide the member with an extended or retracted length. The telescoping capability may be advantageous in small areas where the size of a standard overhead tube suspension X-ray system would be prohibitive. In other embodiments, having one or more extended length members would be advantageous to provide a larger coverage area. In some embodiments, the robotic arm may have a vertical travel of approximately 1500 mm and in at least one embodiment may be extendable to a length of approximately 2700 mm. FIG. 3 shows a side view of a typical radiology suite and a corresponding side view 805 of an exemplary coverage area 800 having a radius of 2700 mm provided by the robotic arm. The combination of joints and telescoping arms of the robotic arm 300 provides for an enhanced scanning ability, for example, along a longitudinal path as shown by arrows 825. FIG. 4 shows a top view of the typical radiology suite and a top view 810 of the 2700 mm coverage area 800. The combination of joints and telescoping arms of the robotic arm 300 provides for a further enhanced scanning ability, for example, along a lateral path as shown by arrows 830. It is clear that the joints and telescoping arm members of the robotic arm 300 provide an enhanced coverage area that includes the entire surface of the table 500 and the entire surface of the wall stand 600.

Figure 5:
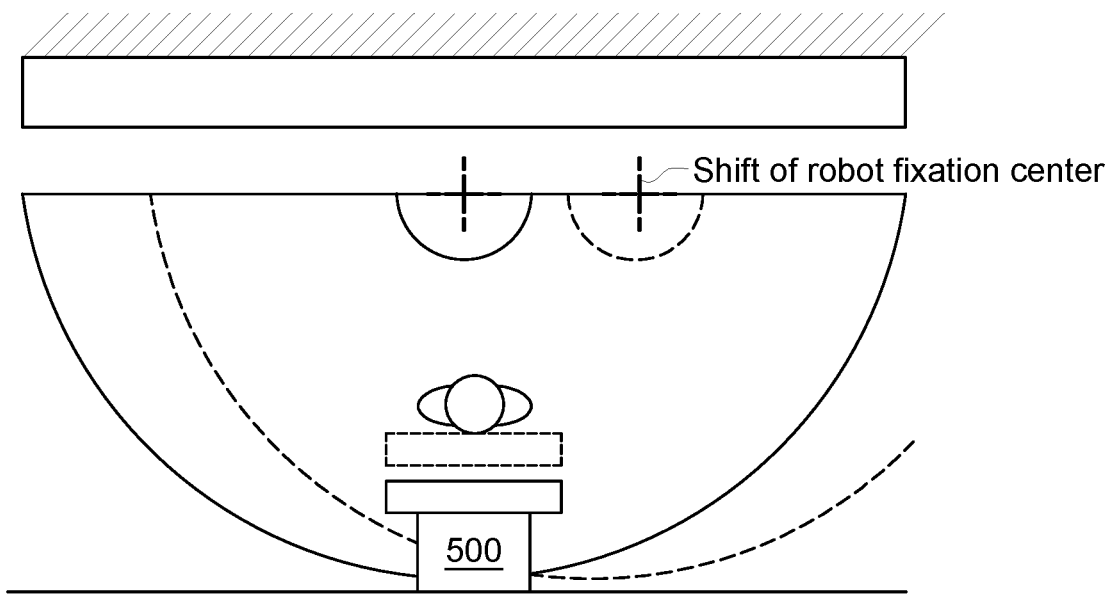
FIG. 5 shows a coverage area provided under two exemplary scenarios of table top position, source to image-receptor distance (SID), and robotic arm fixation distance from a ceiling.
Figure 6:
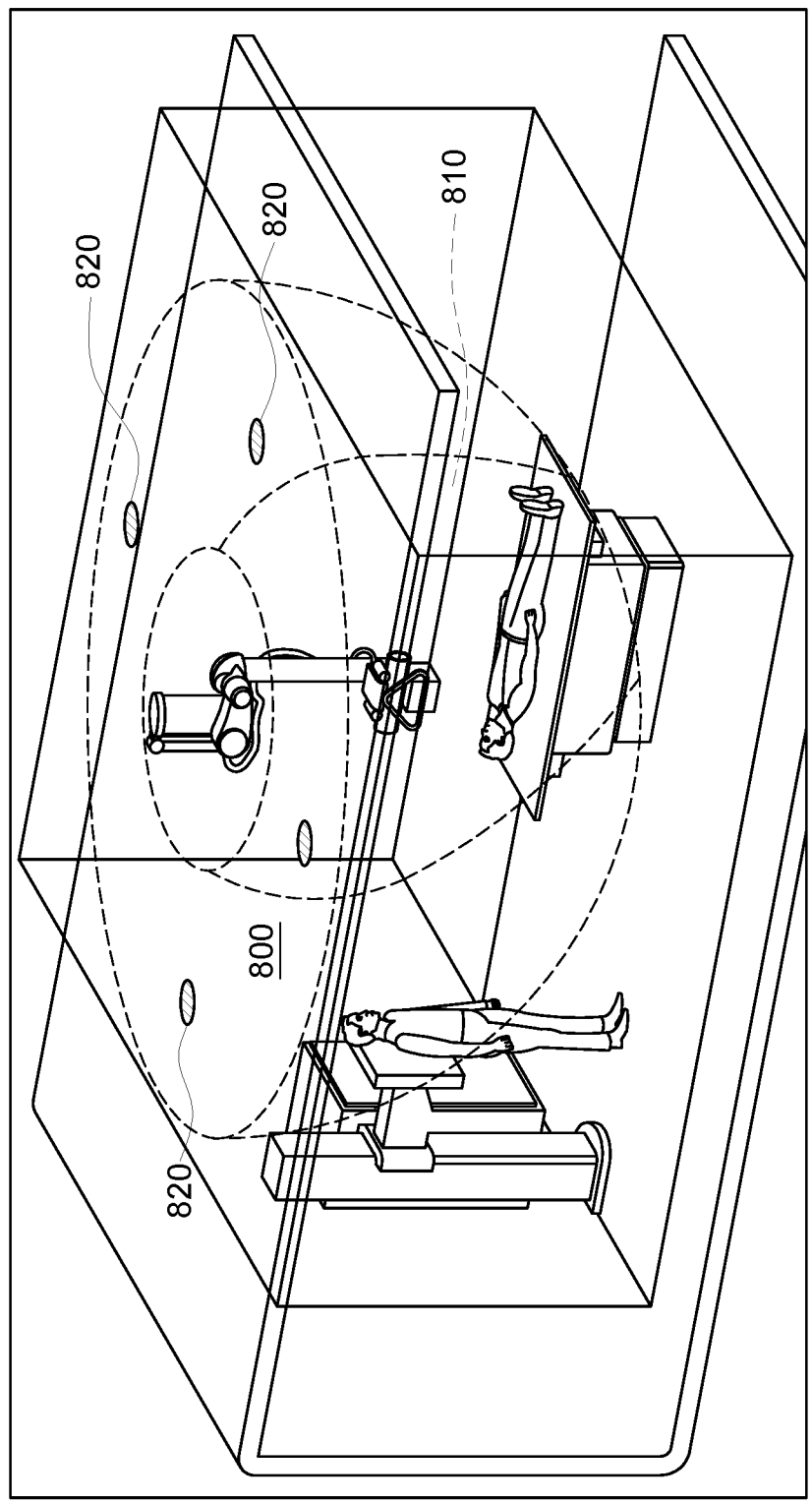
FIGS. 6 and 7 show three dimensional outlines of a coverage area within a radiology suite from different perspective views.
Figure 7:
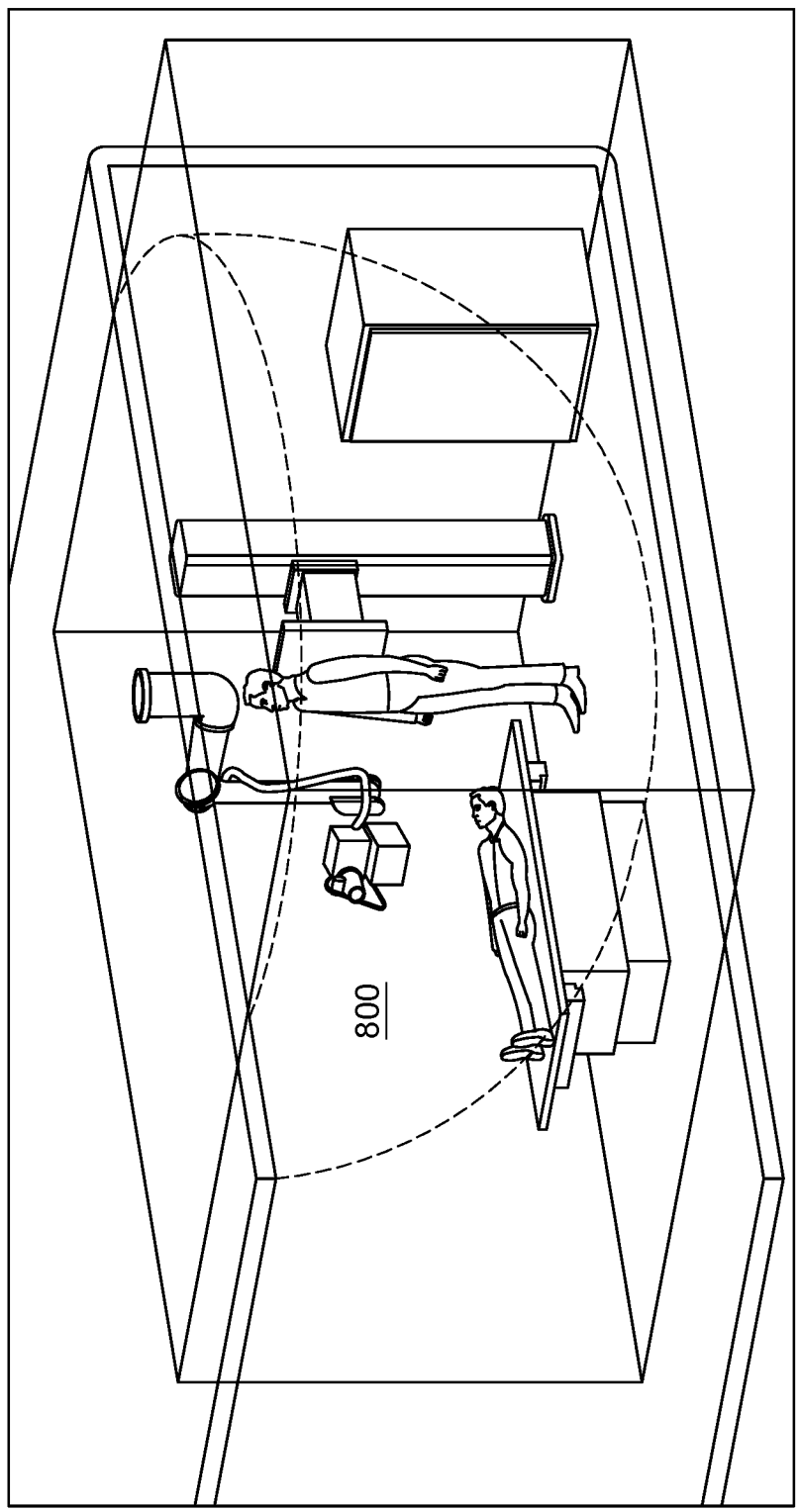

FIG. 5 shows that the robotic arm provides more than adequate coverage under two worst case scenarios including table top position, source to image-receptor distance (SID), and robotic arm fixation distance from the ceiling. In one worst case scenario, the table 500 is at a topmost position of 830 mm above the floor, the maximum SID required is 1500 mm, and the robotic arm 300 is mounted 300 mm below the ceiling, resulting in a required coverage distance of 2630 mm, well within the 2700 mm coverage distance provided by the robotic arm 300. In another worst case scenario, the table 500 is at a lowest position of 500 mm above the floor, the minimum SID required is 900 mm, and the robotic arm 300 is mounted 200 mm below the ceiling, resulting in a required coverage distance of 1600 mm, again well within the 2700 mm coverage distance provided by the robotic arm 300. FIGS. 6 and 7 show three dimensional outlines of the coverage area 800 within the radiology suite from different perspective views.

Returning to FIG. 2, each joint 305, 310, 320, 330, 340, 345, base arm member 315, upper arm member 325, lower arm member 335 and end effector 350 may be configured to provide a power assisted manual movement of the robotic arm 300. The robotic arm may be moved manually by an operator in a power assisted mode, and may include sensors and motors at each joint and arm member that sense an application of external force and respond with movement in the force direction while the force is being applied. Each motor of the robotic arm 300 may have a torque control mode loop that operates to sense the external force and provide a responding force. The manual movement of the robotic arm 300 may be recorded by the work station for use during radiology procedures. The power assisted mode may provide the operator with the ability to move the X-ray source mounted on the end effector along a shorter, more direct path from an initial or parked position to a scanning position. The power assisted mode may also provide the operator with the ability to move the X-ray source mounted on the end effector directly along a more efficient scanning path during scanning procedures. The effective scanning speed of the X-ray source may also be enhanced because of the more direct path and also because the robotic arm may transport the end effector faster than the conventional overhead tube suspension systems.

Cabling, including signal and power lines for operating the robotic arm 300 may be routed internally within the arm 300, or may be flexibly attached to exterior portions of the robotic arm 300 (FIGS. 6 and 7). While the robotic arm 300 is described as having six joints and three arm members, it should be understood that the robotic arm 300 may have any number of joints and any number of arm members suitable for positioning and orienting the X-ray source 355. The joints and arm members may operate under control of the work station 400 to automatically move the end effector 350 and the X-ray source 355 at various speeds, for example, from 1 mm/sec to 500 mm/sec, and may provide at least a 2000 mm patient coverage length, an SID of 1800 mm, including, for example, a 1300 mm SID for wall stand applications and a 1000-1500 mm SID for table applications.

After installation, the robotic arm 300 may generally occupy less surface space than conventional overhead tube and suspension systems because the waist joint may serve as the mounting point as opposed to a complex system of rails on which a bridge may be mounted. In some embodiments, the reduction in occupied surface space may be at least 20%.

The work station 400 may include a computer 405, one or more input devices 410, for example, a keyboard, mouse, or other suitable input apparatus, and one or more output devices 415, for example, display screens or other devices providing data from the work station 400. The work station 400 may receive commands, scanning parameters, and other data from an operator or from a memory 430 and processor 425 of the computer 405. The commands, scanning parameters, and other data may be used by the computer 405 to exchange control signals, commands, and data with the robotic arm 300, the table 500, the wall stand 600, and the detector 700 through a control interface 435 connected to the components of the fixed X-ray system 200. For example, the control interface 435 may provide control signals for the X-ray generator 355*a*, the collimator 355*b*, the detector 700, and control signals for the robotic arm 300. The control interface 435 may further provide control signals for the table 500 and wall stand 600.

The work station 400 may control the frequency and amount of radiation produced by the X-ray source 355, the sensitivity of the detector 700, and the positions of the table 500 and wall stand 600 in order to facilitate scanning operations. Signals from the detector 700 may be sent to the work station 400 for processing. The work station 400 may include an image processing capability for processing the signals from the detector to produce an output of real time 2D or 3D images for display on the one or more output devices 415.

In at least one embodiment, the work station 400 may compute trajectories for the robotic arm 300 in response to scanning procedures provided by a user or stored in memory 430, and provide signals to the robotic arm 300 to implement those trajectories. The work station 400 may also use the recorded manual movements of each joint 305, 310, 320, 330, 340, 345, base arm member 315, upper arm member 325, lower arm member 335 and end effector 350 to calculate trajectories for the robotic arm 300. Referring to FIG. 6, using the computed trajectories, the work station 400 may define one or more exemplary work zones in which the robotic arm 300 travels within coverage area 800 to perform one or more scanning procedures. The exemplary fixed X-ray system 200 according to the disclosed embodiments may include one or more sensors 820 for sensing objects that may be within the work zone. In some embodiments, the work zone may be movable and may change dynamically. For example, the work zone may be determined with respect to a proximity to the X-ray source 355 as the X-ray source travels through the radiology suite. The sensors 820 may be coupled to the work station which may operate to re-compute one or more trajectories, slow the robotic arm assembly 300, stop the robotic arm assembly 300, or otherwise control the robotic arm assembly 300 to avoid possible collisions. The computed trajectories may provide more efficient and faster movement of the X-ray source along a direct path to a scanning position in space, as opposed to prior art overhead tube suspension systems. For example, one or more computed trajectories may provide a shorter, more direct path for the X-ray source mounted on the end effector, when traveling from an initial, or parked position to a scanning position.

The table 500 may be motorized and capable of movement in any number of directions. The table may include a bucky 510 or other device for holding a detector 700. The work station 400 may operate the table 500 to locate a patient in a particular position or orientation with respect to the X-ray source 355 during a scanning procedure, for example, the table may be positioned from approximately 500 mm to approximately 830 mm above a floor on which the table may be mounted. The work station 400 may also operate to receive signals from the detector 700 for generating images resulting from the scanning procedures.

The wall stand 600 may include a laterally projecting member 605 mounted on a vertical stanchion 610. The laterally projecting member 605 may be vertically adjustable and may be fixed at any suitable height. A distal end of the laterally projecting member 605 may include a tiltable bucky 615 for holding the detector 700.

The detector 700 may be a digital radiography receiver panel and may have a two dimensional detection plane for detecting X-rays. The detector 700 may be coupled to the work station 400 and may provide image data from scanning procedures in real time. In some embodiments, the detector may have a wireless communication capability and may be coupled wirelessly to the work station 400. In one or more embodiments, the detector 700 may store imaging data and output the imaging data when subsequently coupled to the work station 400. While shown separately in FIG. 2, the detector may generally be mounted in a bucky 510, 615 during use.

The disclosed embodiments advantageously provide a fixed X-ray system that includes an X-ray source mounted on a multiple degree of freedom robotic arm having telescoping arm members. The fixed X-ray system includes a collision avoidance system for avoiding contact between the robotic arm and other objects within a radiology suite in which the system is installed. The telescoping capability provides for installation in small areas where the size of a standard overhead tube suspension X-ray system would be prohibitive, as well as installation in larger areas where having an extended coverage area would be advantageous. The disclosed fixed X-ray system provides coverage over a range of radiology suite parameters, including a minimum and maximum table height, a minimum and maximum SID, and a minimum and maximum below the ceiling mounting height for the robotic arm. The multiple joints and telescoping arm members of the robotic arm provide an enhanced ability to obtain images from points of view that re not possible using overhead tube suspension systems. For example, the disclosed robotic arm design provides an ability to perform complex x-ray imaging procedures which may include complex tomography procedures and may be especially useful for imaging trauma cases.

The disclosed fixed X-ray system may also provide a power assisted manual movement mode where sensors and motors at each joint and arm member may sense an application of external force and respond with movement in the force direction while the force is being applied. The joints and arm members may operate under control of a work station to move the end effector at various speeds, and over various paths that provide a faster and more direct scanning path than conventional overhead tube support systems. The work station may compute trajectories for the robotic arm in response to scanning procedures provided by a user or stored in memory, or may use recorded manual movements from the power assisted manual movement mode.

Various modifications and adaptations may become apparent to those skilled in the relevant arts in view of the foregoing description, when read in conjunction with the accompanying drawings. However, all such and similar modifications of the teachings of the disclosed embodiments will still fall within the scope of the disclosed embodiments.

While the invention has been described with reference to exemplary embodiments, it will be understood by those skilled in the art that various changes may be made and equivalents may be substituted for elements thereof without departing from the scope of the invention. Furthermore, the skilled artisan will recognize the interchangeability of various features among different embodiments and that various aspects of different embodiments may be combined together. Similarly, the various method steps and features described, as well as other known equivalents for each such methods and feature, can be mixed and matched by one of ordinary skill in this art to construct additional assemblies and techniques in accordance with principles of this disclosure. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

Furthermore, some of the features of the exemplary embodiments could be used to advantage without the corresponding use of other features. As such, the foregoing description should be considered as merely illustrative of the principles of the disclosed embodiments and not in limitation thereof.

The invention claimed is:

1. An X-ray system comprising:
a multiple degree of freedom robotic arm mounted to a surface of a radiology suite, the robotic arm having a plurality of telescoping arm members, wherein the plurality of telescoping arm members includes at least three arm members comprising a base arm member, an upper arm member, and a lower arm member each having independent telescoping capability;
an X-ray source mounted on an end effector of the multiple degree of freedom robotic arm;
at least one X-ray detector; and
a work station coupled to the robotic arm, X-ray source, and X-ray detector, wherein the work station is configured to compute robotic arm trajectories for at least one scanning procedure and to control the robotic arm, X-ray source, and X-ray detector to effect the at least one scanning procedure;
wherein the plurality of telescoping arm members of the robotic arm are independently rotatable around an axis, extendable and retractable to provide an X-ray source coverage area corresponding to dimensions of the radiology suite.

2. The X-ray system of claim 1, further comprising one or more of a movable table and a movable wall stand in which the X-ray detector is mounted, and wherein the work station is further configured to control movement of the one or more of a movable table and a movable wall stand to effect the at least one scanning procedure.

3. The X-ray system of claim 1, wherein the multiple degree of freedom robotic arm is mounted to one or more of a ceiling, a wall, or a floor of the radiology suite.

4. The X-ray system of claim 1, wherein the multiple degree of freedom robotic arm comprises a plurality of joints providing six degrees of freedom.

5. The X-ray system of claim 1, wherein the X-ray source comprises an X-ray generator and an X-ray collimator.

6. The X-ray system of claim 1, wherein the X-ray detector comprises a digital radiography receiver panel with a two dimensional detection plane.

7. The X-ray system of claim 1, wherein the X-ray detector is configured to provide image data to the work station in real time.

8. The X-ray system of claim 1, wherein the X-ray detector is configured to store image data and output the image data when coupled to the work station.

9. The X-ray system of claim 1, wherein the work station is configured to provide signals for controlling a frequency and amount of radiation produced by the X-ray source during scanning operations.

10. The X-ray system of claim 1, wherein the work station is configured provide signals for controlling a sensitivity of the detector during scanning operations.

11. The X-ray system of claim 1, wherein the work station comprises an image processing capability for processing the signals from the detector to produce an output of 2D or 3D images from the scanning operations.

12. A method of X-ray imaging comprising:
   mounting a multiple degree of freedom robotic arm to a surface of a radiology suite, the robotic arm having a plurality of telescoping arm members, wherein the plurality of telescoping arm members includes at least three arm members comprising a base arm member, an upper arm member, and a lower arm member each having independent telescoping capability;
   mounting an X-ray source on an end effector of the multiple degree of freedom robotic arm;
   providing at least one X-ray detector positioned to receive radiation produced by the X-ray source;
   computing robotic arm trajectories for at least one scanning procedure and controlling the robotic arm, X-ray source, and X-ray detector to effect the at least one scanning procedure;
   independently rotating around an axis, extending and retracting the plurality of telescoping arm members of the robotic arm to provide an X-ray source coverage area corresponding to dimensions of the radiology suite.

13. The method of X-ray imaging of claim 12, comprising controlling movement of one or more of a movable table and a movable wall stand holding the detector to effect the at least one scanning procedure.

14. The method of X-ray imaging of claim 12, comprising controlling a frequency and amount of radiation produced by the X-ray source during scanning operations.

15. The method of X-ray imaging of claim 12, comprising using the X-ray detector to provide image data to the work station in real time.

16. The method of X-ray imaging of claim 12, comprising using the X-ray detector to store image data and output the image data when coupled to the work station.

17. The method of X-ray imaging of claim 12, comprising processing the signals from the X-ray detector to produce an output of 2D or 3D images from the scanning operations.

* * * * *